(12) United States Patent
Olguin Alvarez et al.

(10) Patent No.: US 11,331,040 B2
(45) Date of Patent: May 17, 2022

(54) COMMUNICATION USING PROGRAMMABLE MATERIALS

(71) Applicant: Logicink Corporation, San Francisco, CA (US)

(72) Inventors: Carlos Edel Olguin Alvarez, San Francisco, CA (US); Skylar Jackson Eagle Tibbits, Boston, MA (US); Marcelo Henrique Coelho, Boston, MA (US); Tal Danino, New York, NY (US)

(73) Assignee: Logicink Corporation, San Francisco, CA (US)

( * ) Notice: Subject to any disclaimer, the term of this patent is extended or adjusted under 35 U.S.C. 154(b) by 355 days.

(21) Appl. No.: 15/451,065

(22) Filed: Mar. 6, 2017

(65) Prior Publication Data

US 2017/0325737 A1 Nov. 16, 2017

Related U.S. Application Data

(60) Provisional application No. 62/275,215, filed on Jan. 5, 2016.

(51) Int. Cl.
*A61B 5/00* (2006.01)
*G01N 27/327* (2006.01)
*A61B 5/145* (2006.01)

(52) U.S. Cl.
CPC ........ *A61B 5/4845* (2013.01); *A61B 5/14517* (2013.01); *A61B 5/6832* (2013.01); *G01N 27/327* (2013.01); *A61B 2562/0214* (2013.01)

(58) Field of Classification Search
CPC .... A61K 8/0208; A61Q 1/025; A61B 5/4845; A61B 5/14517; A61B 5/6832; A61B 2562/0214; G01N 27/327
See application file for complete search history.

(56) References Cited

U.S. PATENT DOCUMENTS 4,382,063 A * 5/1983 Romito ................ G01N 31/226
116/207
4,788,432 A 11/1988 Patel
(Continued)

FOREIGN PATENT DOCUMENTS

WO WO 02/094098 11/2002
WO WO 2012/074509 6/2012
(Continued)

OTHER PUBLICATIONS

PCT/US18/16281, Cumulative Biosensor System to Detect Alcohol, filing Date : Jan. 31, 2018.
(Continued)

*Primary Examiner* — Patrick Fernandes
(74) *Attorney, Agent, or Firm* — Polsinelli LLP (57) ABSTRACT

A dynamic sensor interface is provided. Such a dynamic sensor interface may include a reaction portion that includes a biological-based or chemical-based ink. Such ink reacts in response to a molecule of interest. The dynamic sensor interface may further include an electrode that detects the reaction by the ink in response to the molecule of interest, as well as a signal interface that emits a signal based on the electrode detecting the reaction. Such a dynamic sensor interface allows for information to be detected and communicated through and between both bio-chemical and electronic systems.

15 Claims, 6 Drawing Sheets

(56) References Cited

U.S. PATENT DOCUMENTS

| | | | |
|---|---|---|---|
| 5,899,856 | A | 5/1999 | Schoendorfer et al. |
| 6,251,083 | B1 | 6/2001 | Yum et al. |
| 6,267,724 | B1 | 7/2001 | Taylor |
| 6,706,099 | B2 | 3/2004 | Sir et al. |
| 6,773,671 | B1* | 8/2004 | Lewis ............... G01N 33/521 422/169 |
| 7,969,307 | B2 | 6/2011 | Peeters |
| 9,131,893 | B2 | 9/2015 | Faybishenko et al. |
| 9,532,762 | B2 | 1/2017 | Cho et al. |
| 10,195,294 | B2 | 2/2019 | Tibbits |
| 2006/0206180 | A1* | 9/2006 | Alcidi ............... A61N 1/403 607/102 |
| 2007/0160814 | A1 | 7/2007 | Mercolino |
| 2008/0107699 | A1 | 5/2008 | Spigelman et al. |
| 2009/0050491 | A1* | 2/2009 | Brown ............... C12Q 1/006 205/777.5 |
| 2009/0325221 | A1 | 12/2009 | Long et al. |
| 2010/0140108 | A1* | 6/2010 | Roblin ............... G01N 27/327 205/775 |
| 2011/0106000 | A1 | 5/2011 | Jones et al. |
| 2011/0295091 | A1* | 12/2011 | Azer ............... G16H 40/67 600/309 |
| 2012/0165626 | A1 | 6/2012 | Irina et al. |
| 2012/0187000 | A1* | 7/2012 | Kahn ............... G01N 27/3335 205/782 |
| 2015/0126834 | A1 | 5/2015 | Wang et al. |
| 2016/0339120 | A1 | 11/2016 | Tibbits |
| 2017/0071536 | A1 | 3/2017 | Tibbits |
| 2017/0186160 | A1 | 6/2017 | Satish et al. |
| 2020/0022648 | A1 | 1/2020 | Danino |

FOREIGN PATENT DOCUMENTS

| | | |
|---|---|---|
| WO | WO 2015/159280 | 10/2015 |
| WO | WO 2016/025468 | 2/2016 |
| WO | WO 2016/090189 | 6/2016 |
| WO | WO 2018/144627 | 8/2018 |

OTHER PUBLICATIONS

U.S. Appl. No. 15/358,415 Final Office Action dated Mar. 29, 2019.
Danino et al., "A synchronized quorum of genetic clocks," Nature, 2010, pp. 326-330, plus 9 pgs. of Supplementary Information, vol. 463.
Jia et al., "Electrochemical Tattoo Biosensors for Real-Time Noninvasive Lactate Monitoring in Human Perspiration" Analytical Chemistry 2013, 85: 6553-6560.
Lei et al., "Microbial Biosensors; Analytica Chimca Acta" 568 (2006) 200-210.
Prindle et al., "A Sensing array of radically coupled genetic 'biopixels'," Nature, 2012, pp. 39-44,vol. 481.
U.S. Appl. No. 15/162,438 Office Action dated Jan. 23, 2017.
PCT Application No. PCT/US2018/016281 International Search Report and Written Opinion dated May 29, 2018.
Bjerketorp et al., "Advances in preservation methods: Keeping biosensor microorganisms alive and active," Current Opinion in Biotechnology, 2006, 17:43-49.
MacNab et al., "The Gradient-Sensing Mechanism in Bacterial Chemotaxis", Proc. Nat. Acad. Sci. USA, vol. 69, No. 9, pp. 2509-2512.
Martinez et al., "Three-dimensional microfluidic devices fabricated in layered paper and tape." PNAS 105(50): 19606-19611, 2008.
U.S. Appl. No. 15/162,438 Final Office Action dated Jul. 11, 2017.
Bartolo et al., Microfluidic Stickers; Lab on a Chip 8:274-279) (Year:2007).
U.S. Appl. No. 15/358,415 Office Action dated Sep. 19, 2017.
U.S. Appl. No. 15/162,438 Office Action dated Apr. 10, 2018.
U.S. Appl. No. 15/358,415 Final Office Action dated Apr. 9, 2018.
U.S. Appl. No. 15/358,415 Office Action dated Nov. 2, 2018.
U.S. Appl. No. 16/268,430, Skylar J.E. Tibbits, Programmable Bacterial Tattoo, filed Feb. 5, 2019.
U.S. Appl. No. 16/528,362, Tal Danino, Cumulative Biosensor System to Detect Alcohol, filed Jul. 31, 2019.
U.S. Appl. No. 15/358,415 Final Office Action dated Aug. 23, 2018.
U.S. Appl. No. 15/358,415 Final Office Action dated Mar. 11, 2020.
U.S. Appl. No. 15/358,415 Final Office Action dated Sep. 28, 2020.
PCT Application No. PCT/US2018/016281 International Preliminary Report on Patentability dated Aug. 6, 2019; 6 pages.
Koh, Ahyeon, et al., "A soft, wearable microfluidic device for the capture, strange, and colorimetric sensing of sweat," Nov. 23, 2016, Science Translational Medicine, 8(366), https://stm.sciencemag.org/content/8/366/366ra165.full (Year:2016).
Supplementary Materials for A soft, wearable microfluidic device for the capture, strange, and colorimetric sensing of sweat. Science Translational Medicine, Nov. 23, 2016. 25 pages.
U.S. Appl. No. 15/358,415 Final Office Action dated May 6, 2021.
U.S. Appl. No. 16/528,362 Office Action dated Apr. 23, 2021.
U.S. Appl. No. 16/528,362 Final Office Action dated Aug. 31, 2021.

* cited by examiner

COMMUNICATION USING PROGRAMMABLE MATERIALS

CROSS-REFERENCE TO RELATED APPLICATIONS

The present application claims the priority benefit of U.S. provisional application No. 62/275,215 filed Jan. 5, 2016, the disclosure of which is incorporated herein by reference.

BACKGROUND OF THE INVENTION

Field of the Disclosure

This disclosure relates generally to sensor interfaces. In particular, the disclosure relates to communication with biological-based and chemical-based sensor interfaces.

Description of the Related Art

Sensors may be used to detect various types of information regarding a person, object, or environment. Presently available sensors are generally mechanical in nature. Such mechanical sensors may include a variety of mechanical components based on the type of stimuli or other information being sensed, measured, and reported. As such, mechanical sensors are generally bulky, heavy, cumbersome, or otherwise uncomfortable and inconvenient to wear or carry. Smaller mechanical sensors, on the other hand, may lack accuracy or lack ability to convey much information beyond a binary indication. Such sensors may be unable, for example, to indicates changes that occur over time, changes in behavior, or other characteristics.

In addition, mechanical sensors may often require an external power sources (e.g., battery), which limits the scalability of the sensor given the bulky nature of batteries, wires, and other power input accessories. Similarly, power requirements constrain the applications given the risk of harming the user with overheating, failed batteries, shock or other types of electrical failure. Notwithstanding, the vast majority of computing devices in existence rely on electrical signals and communications.

There is, therefore, a need in the art for improved systems and methods for communication using programmable materials that are biological-based or chemical-based.

SUMMARY OF THE CLAIMED INVENTION

A dynamic sensor interface device is provided. Such a dynamic sensor interface may include a reaction portion that includes a biological-based or chemical-based ink. Such ink reacts in response to a molecule of interest. The dynamic sensor interface may further include an electrode that detects the reaction by the ink in response to the molecule of interest, as well as a signal interface that emits a signal based on the electrode detecting the reaction. Such a dynamic sensor interface allows for information to be detected and communicated through and between both bio-chemical and electronic systems.

DETAILED DESCRIPTION

A dynamic sensor interface device is provided. Such a dynamic sensor interface device may include a reaction portion that includes a biological-based or chemical-based ink. Such ink reacts in response to a molecule of interest. The dynamic sensor interface may further include an electrode that detects the reaction by the ink in response to the molecule of interest, as well as a signal interface that emits a signal based on the electrode detecting the reaction. Such a dynamic sensor interface allows for information to be detected and communicated through and between both bio-chemical and electronic devices and systems.

In addition, such a dynamic sensor interface device may communicate with other sensor interface devices using their respective sensing, processing, and actuating capabilities that a biologically or chemically programmed material is selected to exhibit. In a first exemplary embodiment, a first device may send a message by exhibiting one or more characteristics that is recognized by the other device. For example, a first sensor device may emit an olfactory signal, releasing aromatic molecules into the air. Such molecules may act as stimuli to another sensor device that is within range to detect the same. Such stimuli may also be detected as any combination of physical, tactile, chemical, and biological changes, including changes in temperature, light, moisture, acidity, or concentrations of a certain molecular species. The programmable material can be near, on, or in the second entity when displaying back the information received. The act of displaying back information may include changes in shape, color, texture, temperature, smell, taste, speed of movement, direction, degree of change, and other behavior or means.

In other embodiments, an individual may input a message by interacting with the programmable material. Such interaction may include any combination of applying pressure, covering, exhaling, uttering sounds, relaxing or tensing muscles, drinking, eating, sleeping, etc. The message or signal may result in programmed reactions by the programmable material. Such reactions may take the form of detectable, measurable changes, which may then be encoded for and sent to another device. The type of encoding is based on the type of receiving device and the type of signals such receiving device is capable of detecting. For example, where the receiving device is an electronic device (e.g., mobile communication device or smartphone), the signal may be a wireless electronic signal. Where the receiving device is another biologically- or chemically-based sensor device, the stimuli may take the form of an emitted biological or chemical molecule.

When such sensor interface device receives a signal, the device may then decode the signal and present a notification of the same. Where the receiving device is electronic, such notification may be an electronic display on a screen. Where the receiving device is biologically- or chemically-based, such notification may take the form of biological or chemical reactions that result in perceptible changes (e.g., color change). A sensor interface device may communicate with other sensor interface devices, as well as with electronic devices. A sensor interface device may therefore communicate with its wearer's other devices (e.g., electronic device), as well as with devices belonging to others (including both other biological or chemical sensor interface devices and electronic devices).

In that regard, two communicating entities may send and receive messages by interacting with a programmable material (e.g., in a sensor interface device) near, on, or within the respective entity. A conventional communication system (e.g., electronic) may be used to transmit the message across long or short distances. In some embodiments, such communicating entities may rely solely on their interaction with respective programmable materials to send and receive messages to each other. As such, a sensor-agnostic process may be provided for alerting users of incremental changes in their state of health, negative or positive.

Figure 1:
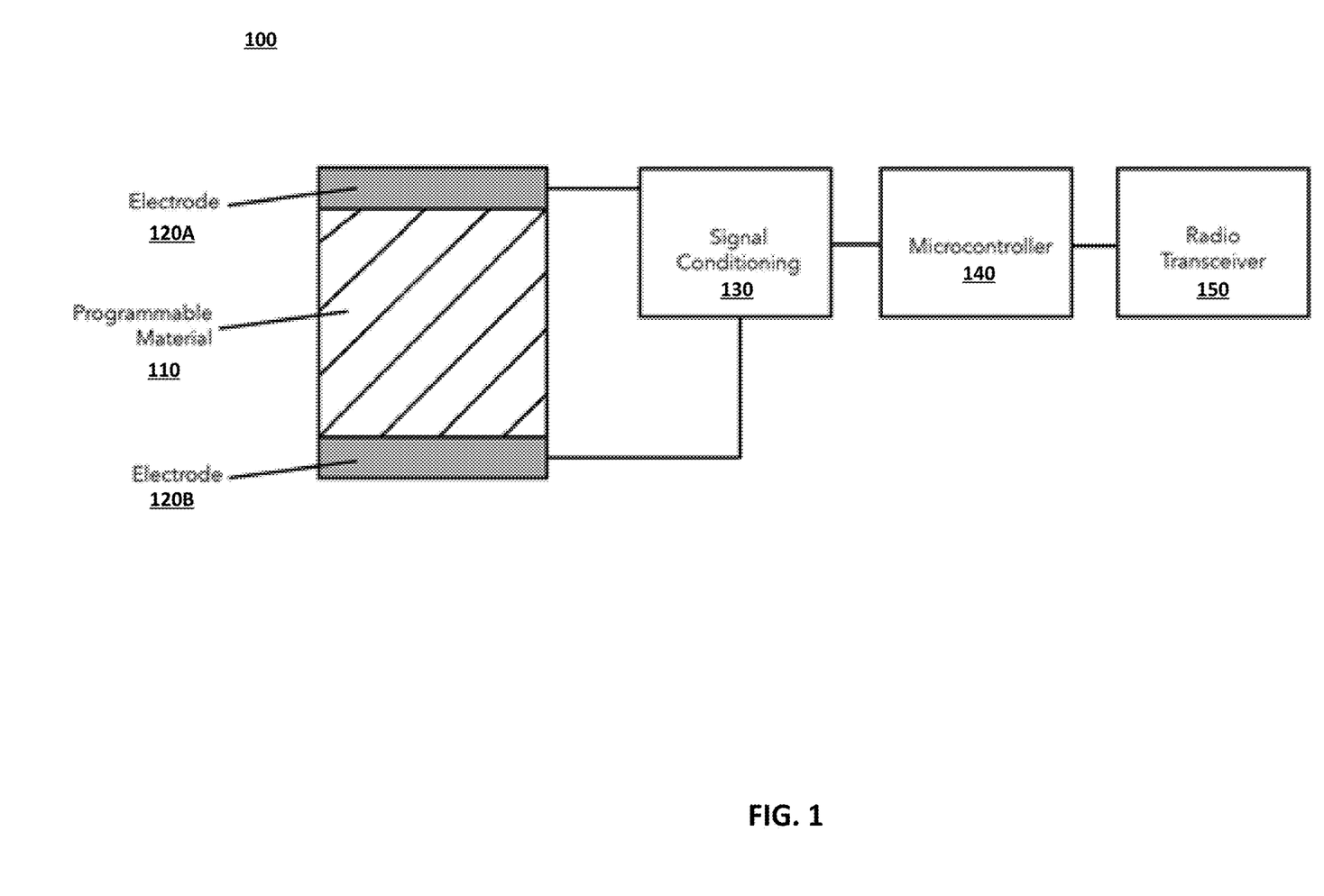
FIG. 1 illustrates an exemplary structure for a wearable biological or chemical-based sensor interface device.

FIG. 1 illustrates an exemplary structure for a wearable biological or chemical-based sensor interface device 100. Such a sensor interface device 100 may include a reaction portion 110 (that includes programmable material), one or more electrodes 120A-B, a signal conditioning circuit 130, a microcontroller 140, and a signal interface 150 (e.g., radio transceiver).

Such a dynamic sensor interface device 100 may be temporarily adhered to a variety of different surfaces, including skin, clothing, packaging, etc. As such, the sensor interface device 100 may include various adhesive substrates, seals, and layers that permit for adhesion to various surfaces (e.g., skin), containment of the function ink(s) (described in further detail with respect to the reaction portion 110), and communication of molecules of interest to the functional inks.

Such a sensor interface device 100 may be used for communications that may be initiated based on detecting the state of a programmable material within the reaction portion 110. Some changes in the reaction portion 110 may be further be perceived through electronic means such as electrodes 120. When electrical changes take place in the programmable material, such as variations in electrical resistance, charge build up or discharge, change in resonant frequency or any other electronically measurable state, these changes are picked up by the electrodes 120. One or more electrodes 120, which may serve as conductors, may be placed within proximity of or in direct contact with the programmable material of the reaction portion 110 so as to detect such changes. The extent of such electrical changes may correlate to the degree of the reaction, thereby providing a measurable change in electrical state that is indicative of the amount of stimuli detected. Such electrical changes may be detected by electrodes 120.

The electrodes 120 may further in communication with signal conditioning circuit 130, which may then transform signals from the electrodes 120 into a readable signal. Such signals may then be read and interpreted by a computer chip or electronic circuit, including microcontroller 140. As such, information indicative of the molecule of interest (e.g., detected presence, amount detected) may be communicated to a microcontroller 140 for analysis, storage, display, and communication (e.g., via radio transceiver 150) to another device. The other device may also communicate via programmable materials (e.g., in a respective reaction portion 110) to the same user or a different user through radio, infrared, or any other standard electronic communication techniques.

Figure 6:
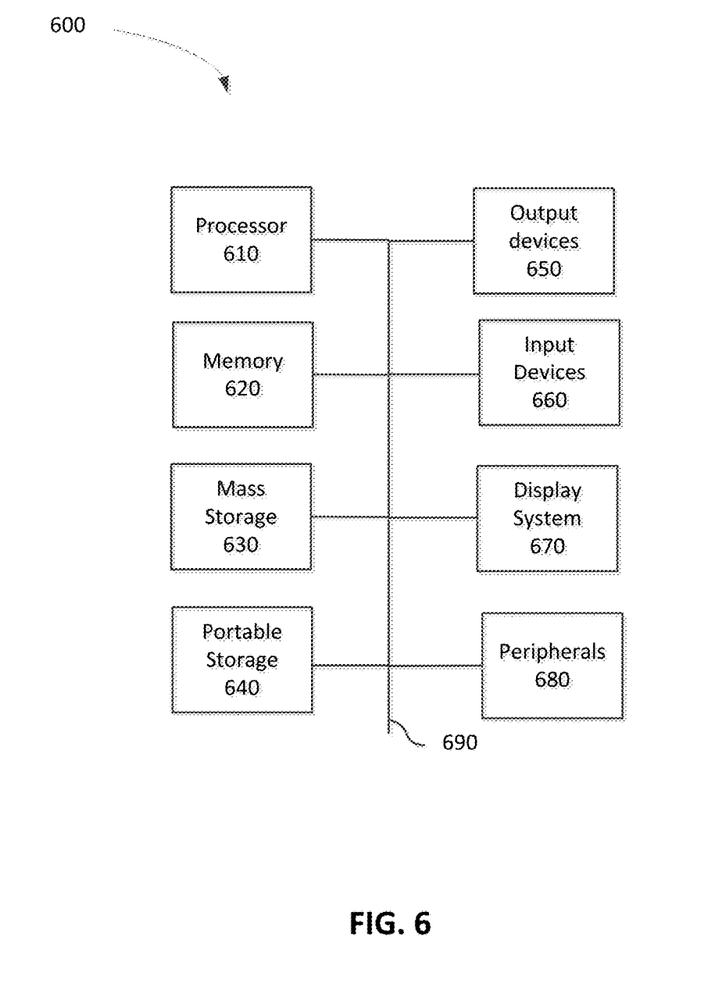
FIG. 6 is a block diagram of an exemplary computing device that may be used to implement an embodiment of the present invention.

Microcontroller 140 may include any type of controller or processor known in the art, such as the processor described with respect to FIG. 6. As such, microcontroller 140 may analyze the indication that the molecule of interest was detected, as well as the amount detected. In some embodiments, the microcontroller 140 may be able to analyze current readings in conjunction with past readings. The results and reports regarding such analyses by microcontroller 140 may be provided to signal interface 150 (e.g., radio transceiver) for transmission to another device. Although FIG. 1 specifically illustrates a radio transceiver—which allows for communication with other devices having radio transceivers, the signal interface 150 is inclusive of biologically- and chemically-based sensor interfaces for emitting biological and chemical signals (e.g., that may act as molecules of interest and react with programmable materials in other sensor interface devices 100).

The reaction portion 110 may be printed or otherwise provided with functional ink, which may be biological-based (e.g., bacterial, dried probiotic) or chemical-based (e.g., cell-free enzyme) or a combination of the same. Such functional ink may be formulated or otherwise engineered to sense a predetermined stimulus (e.g., molecule) of interest that may be found in sweat, other bodily triggers, or the external environment. In some embodiments, the functional inks may be disposed within microfluidic channels within the reaction portion 110.

The reaction portion 110 may include any combination of functional inks, which may be logically structured (e.g., programmed) to react in a way that provides notifications or indicia when one or more stimuli of interest (e.g., molecules such as alcohol, medication, etc.) are detected with respect to internal or external environments. The functional inks react to a predetermined stimulus in a manner that results in a variety of possible transformations. Such transformations may occur with respect to colors, shapes, textures, temperatures, smells, tastes, behaviors, etc., to indicate information to the user or others. The functional ink(s) may be placed in specific arrangements to conceal or display information indicative not just of the stimulus of interest, but other information such as identity, environmental stimuli, biological or health information, exposure time, etc.

The functional ink(s) in the reaction portion 110 may therefore indicate information optically (e.g., changes in visibility/invisibility or color), physically (e.g., ink movement or shape change), behaviorally (e.g., change in speed of movement, direction, degree, etc.); or other indicators (e.g., olfactory, tactile, thermal changes, etc.). Environmental stimuli may include temperature, light, moisture or other factors. User input may include applying pressure, licking, exhaling, uttering sounds, covering the ink, or administering more functional ink.

When the functional ink of reaction portion 110 detects the stimulus of interest, such ink may undergo a perceptible reaction. Such a reaction may include optical changes, movement or behavioral changes, tactile or shape changes, olfactory changes, and thermal changes. Examples of optical changes may include changes in color, transparency (visibility), movement, behavior, shape, and three-dimensional contraction and expansion. A color change may occur, for example, when the functional ink of the reaction portion 110 comes into contact with a particular stimulus, resulting in biochemical reactions that change the color of the functional ink. Color transformation can happen across a range of hues, alpha levels (e.g., from opacity to transparency), or polarization (e.g., similar to an image on a computer screen).

The sensor interface device 100 may include a variety of functional inks disposed in specific ways that allow for communication within the same device, as well as with other device (both electronic and biologically- and chemically-based devices. An exemplary reaction by a wearable biological or chemical-based sensor interface device 100 in response to detected stimuli or other information may include a functional ink of the sensor interface device 100 that may initially appear clear or invisible against the surface to which it adheres before exposure to the stimulus of interest. As the stimulus is sensed, however, the functional ink in the sensor interface device 100 may become visible. The functional ink may then become visible, for example, as sweat or alcohol from skin passes through porous membrane layer to reaction portion 110. In some embodiments, the degree of opacity or transparency may be proportional to the amount of stimulus detected. In some instances, an ink may increase (e.g., fade in) or decrease (e.g., fade out) in prominence in response to a stimulus. The functional ink may be partitioned into a visual interface element.

Another exemplary reaction that may be exhibited by a wearable biological or chemical-based sensor interface device 100 in response to detected stimuli or other information may include a reaction in which an initially invisible functional ink becomes visible. Such a sensor interface device 100 may include nonfunctional ink that appears as two concentric circles, for example. As stimuli are sensed, however, the initially invisible functional ink partitioned between the two concentric circles becomes visible.

In some embodiments, visibility of the functional ink is relative to its background. For example, a particular functional ink may appear red before exposure to a certain stimulus (e.g., UV light), but become blue when exposed to UV light. Graphic interface elements—each utilizing different types of functional and nonfunctional inks partitioned within the reaction portion 110—can appear and disappear in relation to their background. A red flower (functional ink) on a red background (nonfunctional ink), for example, may initially appear invisible until exposed to UV light. The functional ink may then turn the flower blue against the background, which remains red.

In another embodiment, the functional ink may initially be visible before exposure to a stimulus, but disappear when the presence of the stimulus is detected. Depending on the selected functional ink(s) (and nonfunctional inks), such functional ink may either hide or visualize information as an indication or reminder regarding certain stimuli.

In another implementation, the sensor interface device 100 may include one functional ink in channels arranged to form text (e.g. "NO"). As the sensor interface device 100 detects a stimulus, the displayed result may be changed (e.g., "YES"). Such changes may be based on the structure of the channels, as well as the respective inks and ink attributes (e.g. movement, visibility/invisibility). For example, one ink may become invisible, while another ink—that was formerly invisible—may become visible within channels arranged into different text (e.g., "YES"). This allows the interface to transform in appearance into a completely different interface.

Another exemplary reaction by a wearable biological or chemical-based sensor interface device 100 in response to detected stimuli or other information may include movement throughout embedded microfluidic channels in the reaction portion 110. Diffusing through such channels allow the functional ink to go from one configuration to another configuration, completely changing the appearance of the sensor interface. For example, a sensor interface may initially appear as a single line. When a stimulus (e.g., alcohol) is detected, the functional ink within the line may transform into a branching structure. In some cases, the number of branches may indicate a quantitative measurement of how much stimulus (e.g., alcohol) is detected.

When the functional ink senses stimuli in some embodiments, the ink may begin to move throughout embedded microfluidic channels in the reaction portion 110, demonstrating not only a change in appearance of the interface (e.g., moving through different channels) but a behavior change within the interface. The functional ink may begin to move faster, slower, more chaotically, change direction, oscillate, or demonstrate various other behavior changes.

Another exemplary reaction by a wearable biological or chemical-based sensor in response to detected stimuli or other information may include an initial appearance that changes. For example, a circle may appear to be rotating clockwise when there is at least one microfluidic channel structured as a circle, but as the sensor interface device 100 detects a stimulus, the functional ink may escape the circular channel and move outward radially, appearing as a pulsing sunburst.

Changed behavior may occur when the ink is moving faster and more chaotically in reaction to the detected stimulus. In alternative embodiments, other functional inks may move more slowly in reaction to their respective stimuli. Other types of behavioral changes may include oscillation into smaller or larger circles and glowing (e.g., like a power indicator on an electronic device).

In another embodiment, when the functional ink senses stimuli, the ink may begin to change in a three-dimensional manner (e.g., bulging off the skin to create a structure or shape on the user's skin). Such three-dimensional changes may be produced as a result of embedded gasses within the functional ink or that may be produced by the functional ink as a result of stimulus detection. Such reactions may be used to create shapes for tactile notifications. Such functional ink may therefore for (Braille) notifications to visually-impaired users or for an additional level of transformation and embedded information.

Such shape transformation may be created through pressure changes (e.g., off gassing) within arranged channels within the reaction portion 110. Multiple functional inks with three-dimensional expansion or contraction capabilities may be arranged within the reaction portion 110 to create a bimetal effect (e.g., curling or other complex three-dimensional shape changes).

A functional ink that responds to glucose concentration levels, for example, may have an initial state (e.g., prior to stimulus exposure) in which a relatively flat appearance is presented. As increasing glucose levels are detected, the functional ink may expand to create a physical texture indicative of the change in glucose level. The user may therefore be notified of such change via tactile sensation. An undulating 3-dimensional pattern may appear, for example. Further, when a secondary stimulus is sensed, the same or another function ink may create a bulge into a larger convex curve. Such three-dimensional properties may be likewise be arranged so as to present various types of notifications.

In some embodiments, the functional ink exhibits olfactory or thermal changes in reaction to a stimulus. When a functional ink contacts certain stimuli, a particular odor may be produced (e.g., off gassing) that is detectable by the wearer. The odor could be both pleasant, unpleasant or neutral depending on the kind of information the sensor interface seeks to communicate. When a functional ink detects a predetermined level of alcohol, for example, a banana smell may be emitted as a notification of the same.

Thermal changes may also occur when a function ink releases thermal energy to indicate to the user that a certain state has been reached. In some embodiments, the functional ink may detect that a certain level of alcohol has been reached and react to generate heat.

Using various combinations of functional inks—each reacting to specific stimuli in specific ways—a biochemical-based sensor interface may be logically structured (or "programmed") to perform complex functions. The sensor interface may therefore represent a type of biochemical computing platform by which certain inputs (e.g., stimuli) may be detected and processed by functional ink(s), as well as result in useful biochemical transformations.

Functional inks may therefore be analogous to a network engineered as interconnected modules of Boolean circuits. These specialized intermediate compositions of inks may be selected and engineered to embody the behavior of a logical gate (e.g., NOT, AND, NAND, OR, etc.). Such a network may further be interconnected with others to create more sophisticated systems.

As noted above, the functional inks may be formulated or engineered to react with specific internal or external conditions to produce specific biochemical changes. For example, a functional ink may be engineered to detect alcohol (ethanol), glucose, electrolytes, and other conditions. Each functional ink may further have an initial, pre-exposure state, which differs from its respective post-exposure state. As noted above, such states may span various visual/optical, movement/behavioral, tactile/three-dimensional, olfactory, and thermal states. Such states can be set or unset, as well as transmitted or transduced internally or externally to create more sophisticated sensor-processor-actuator systems.

As such, functional inks can be selected based on their capability to oscillate between states. Some functional inks may change from state A to state B, as well as stay at state B indefinitely. For example, a functional ink may detect sunlight and become visible or otherwise visually transform from an initial state (e.g., plain circle) into another state (e.g., intricate sun pattern). Such functional ink may remain in the transformed pattern until the sensor interface device 100 is removed.

Other functional inks may change from state A to B in the presence of stimuli and in the absence of stimuli, revert from state B to state A. For example, a functional ink may detect sweat-alcohol levels above the driving limit and appear as a red "STOP" pattern to indicate that the user is exhibiting elevated alcohol levels and should stop drinking. When the sweat-alcohol level drops below the legal limit, the red "STOP" notification may disappear.

Some functional inks may exhibit multiple discrete and continuous states. For example, a functional ink may transition through multiple states in a discrete fashion, from state A to state B, then from state B to state C, and then from state C back to state A. For example, a sensor interface for detecting ethanol may represent discrete levels of alcohol consumption as a set of stacked bars, including one or more bars designated as beyond a DUI threshold.

The transition may alternatively occur in a continuous fashion (e.g., along a gradient) to represent a plurality of conditions in relation to a stimulus. A sensor interface may include a combination of different functional inks, each detecting a different stimulus relevant to health. Such a sensor interface may therefore be able to reflect an overall state of health (e.g., normal, mild illness, critical) as it aggregates multiple stimuli (e.g., hydration, body temperature, cholesterol, glucose levels). Each stimulus may have a different weight based on arrangement of the respective functional inks in accordance with each stimulus' assigned impact on overall state of health.

In some embodiments, several functional inks may be combined in programming for a conditional compounded measurement. For example, a sensor interface device 100 may include multiple functional inks. A first ink reacts in response to detecting a stimulus (e.g., alcohol), while a second ink reacts in response to detecting another (e.g., prescription medication that may have harmful side effects in the presence of alcohol). In the absence of medication, the first ink may simply produce an indication of alcohol levels. In the absence of alcohol, the second ink may produce an indication of the effectiveness (or other attribute) of the prescription medication. When both inks detect their respective substances, however, the sensor interface device 100 may begin to display a warning symbol.

Another type of combination may allow for path-dependent measurement (e.g., hysteresis). For example, a sensor interface device 100 may also show different states in a conditional fashion—whether compounded or not—when exposed to the same stimuli based on the value of the previous state(s). When so programmed, a glucose biosensor interface may result in a first pattern of a red arrow facing up when glucose levels are high and increasing; when glucose levels are high and decreasing, however, a red arrow facing down may be displayed.

Such a sensor interface device 100 may include three inks: (1) a first ink for detecting alcohol (ethanol) and with an unset state (pre-exposure) where a color is exhibited prominently and a set state (exposure at levels above a predetermined DUI impairment level) where the color fades in prominence; (2) a second ink for detecting hydration level and with an unset state where color fades in prominence when hydration levels are normal and a set state where color increases in prominence when hydration levels fall below a predefined threshold of normalcy; (3) a third ink for detecting the reactions of both of the first two inks and with an unset state where no or little color is exhibited and a set state where color increases in prominence. The first state may be one in which all inks are unset and only the first ink is visible (e.g., state in which no alcohol has been detected and hydration levels are normal). In the second state, only the first ink is set, indicating that alcohol has been detected but hydration levels are still normal. In the third state, only the second ink is set, indicating that hydration levels are below the predefined normal level but no alcohol has been detected. Finally, in the fourth state, all three inks are set, indicating that both alcohol and below-normal hydration levels are detected. As such, the third ink reacts when both alcohol and low hydration levels are detected. Whereas the first ink and the second ink may be reversible (e.g., bi-directional), the third ink may be permanently set (e.g., unidirectional). As such, the third ink may only be reset by replacing the sensor interface device 100. The first ink may be programmed to serve as a less conspicuous notification of DUI levels, since the notification is the absence of color.

The way in which a functional ink transitions from one state to another may be analogous to an LED control. Such transition may be characterized along a sinusoidal wave, square wave, saw tooth, etc. The speed of transition can be immediate or gradual depending on both the levels of detection, transformation speed, external temperature, or other selected factors. For example, a color-changing function ink can oscillate between two different colors at 0.5 Hz to indicate a high level of alcohol concentration, as well as oscillate at 0.1 Hz to indicate a low level of alcohol concentration. In addition, such oscillation can transition from a sinusoidal transformation to a saw tooth one, where the sharper edges in color change may become more visible to the user and serve as an indication that she or he should stop drinking.

A current state may be compared to a previous state by structuring different channels with different reactions. Alternatively, a comparison may be obtained by providing an initial condition spot (e.g., the control) and a secondary spot for the current reaction. The color, shape, movement, or behavior of the ink at the secondary spot can be compare to the control so as to evaluate the extent to which the current condition differs. The user may want to know exactly how different the current state has changed from the initial state over time. For example, two small ink circles may be provided on a sensor interface device 100. One circle may remain constant, while the other circle changes in the presence of a stimulus, allowing for the comparison between the two.

Functional ink can be used to show a change over time, similar in ways to a time-lapse or clock without the need for a comparison to a control. The movement, color change, transparency, or behavior change can be used to indicate the speed or gradual transformation. For example, an ink circle may be provided with incremental channels structured like a clock around the circumference of the circle. As the amount of input stimulus increases, the ink gradually changes color in a clockwise pattern around the circle, filling each of the incremental channels. As such, the ink indicates an amount of stimulus that is sensed over time.

Further, ink can be used to show the speed of a reaction or speed of change with the increase of a stimulus. For example, a circular channel of ink may detect a stimulus and begin to move in a clockwise manner around the channel. When the amount of stimulus increases, the ink may move faster around the circle at a rate corresponding to the speed of change and increase in the quantity of the stimulus.

Functional ink can also be used to show accumulated results, not only the binary state or the speed of a reaction. The user can look at the sensor interface to understand how much of something has been sensed. For example, an ink grid with individual chambers may sense a stimulus, and each one of the individual chambers may change color in an incremental manner based on the quantity or reaction levels sensed. The grid may change color from left-to-right or top-to-bottom, showing an aggregated amount sensed rather than just a snapshot.

A series of channels may be created in the reaction portion 110 and filled with functional ink. Such a series of channels may serve as logic gates so that when a stimulus is sensed, the logic gates become activated. As the functional ink moves through the gates, the resulting reaction adds an amount of input and provides a result in the form of a binary number.

Functional ink can be used to show or conceal private information. A functional ink with a transparency, color, movement, behavior, or other change can help to display information only when subject to a specific stimulus. In this way, the sensor interface can act as a barcode or a hidden user ID. For example, a sensor interface design may indicate a user's blood type, social security number, medical information, or other private information only when a very specific stimulus is applied (e.g., by a medical provider). Similarly, this could be used for validation, authentication, anti-counterfeiting protection, or sending private information from one party to another.

Functional inks can be used in combination with one another or in specific patterns (e.g., to test multiple stimuli at the same time). Rather than providing multiple sensors, a single combination sensor with different inks can be used to test for the presence multiple difference stimuli, thereby facilitating and speeding up testing. Similarly, such a combination sensor can indicate the simultaneous presence of multiple stimuli. Such a combination sensor may be implemented in the medical field, for example, in cases where a patient is being tested for different substances, whether natural or foreign.

Functional ink tattoos can be used to produce another substance in the presence of a stimulus. The reaction created when the sensor interface senses a stimulus can create energy, off gassing, other inks, or some other form of production. For example, a functional ink may sense a stimulus and react by off-gassing, thereby inflating the sensor interface into a 3-dimensional shape. The gas may include a perfume or cologne that is released over time so as to prolong their fragrance over time.

Figure 2:
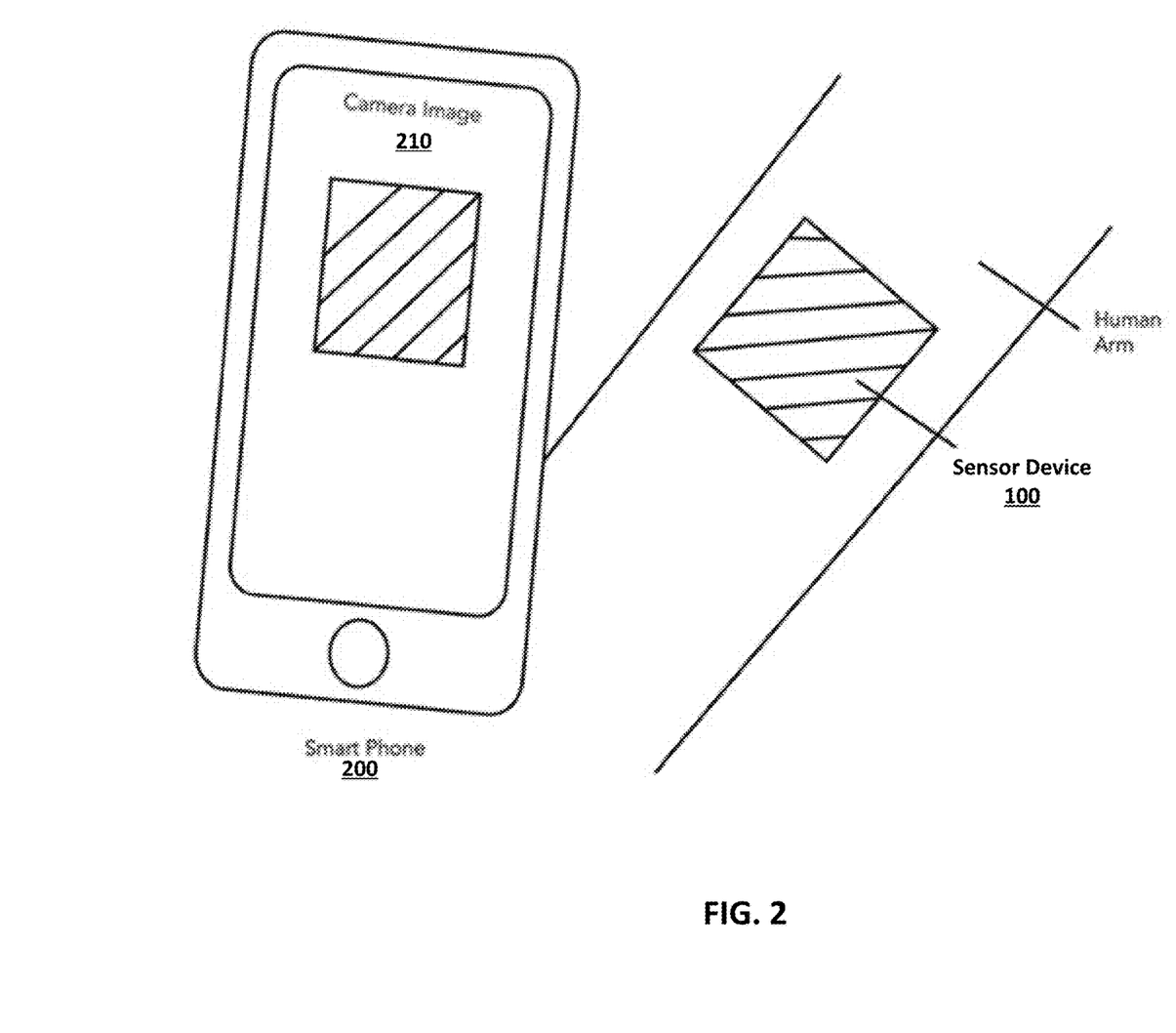
FIG. 2 illustrates an exemplary mobile device that may communicate with the sensor interface device of FIG. 1.

FIG. 2 illustrates an exemplary mobile device 200 that may communicate with the sensor interface device 100 of FIG. 1. In the illustrated implementation, the sensor interface device 100 may be placed on the skin of a wearer (e.g., on the arm). Such sensor interface device 100 may exhibit visual changes that may be perceptible to a camera of mobile device 200. As such, the state of a programmable material of sensor interface device 100 may be exhibited through visual and optical means in such a way that it can be read and interpreted by a computing device 200 (e.g., smart phone or other optically instrumented electronic device).

In one embodiment, the programmable material of sensor interface device 100 may display—in reaction to a detected molecule of interest—a visual pattern that encodes information in a similar fashion to fiducial markers, as well as bar codes, QR codes, and other visually recognizable markers. The computing device 200 can detect such markers by executing a series of pattern detection algorithms, such as known with respect to computer vision.

In another embodiment, the programmable material of sensor interface device 100 can display simple colors and surface changes that can be detected by a camera or other optical sensor operating at non-visible wavelengths (e.g., infrared or ultraviolet), and/or by utilization of time-of-flight depth detection information. The computing device 200 might further provide its own illumination (e.g., IR, UV, "black" light) to read the programmable material state, in which case the illumination might encode specific information that will help in detecting and interpreting the programmable material state. This illumination can be single and multiple source, structured spatially or temporally, and can come from one or many directions.

Figure 3A:
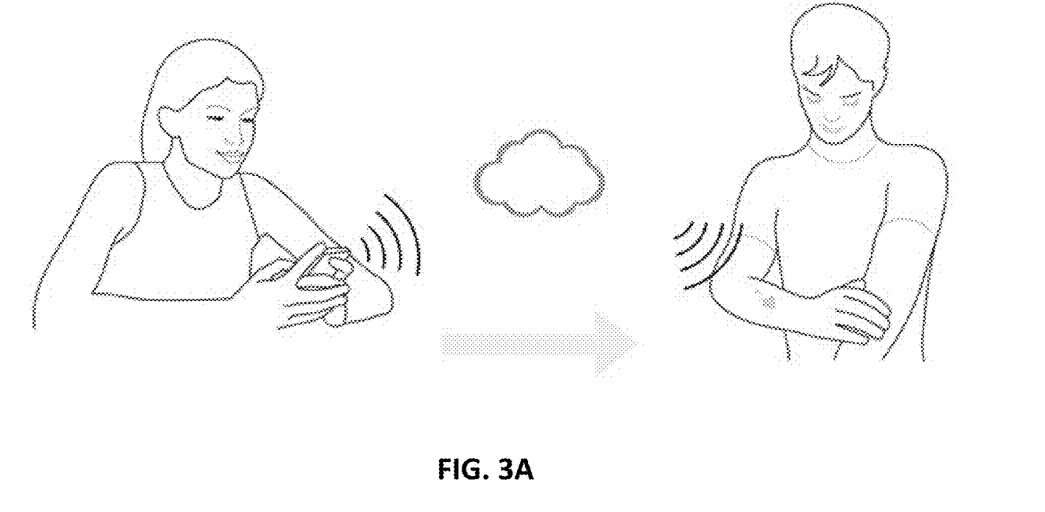
FIG. 3A-3D illustrates a variety of implementations in which a sensor interface device worn by one user may communicate with the sensor interface device worn by another user.

FIG. 3A-3D illustrates a variety of implementations in which a sensor interface device worn by one user may communicate with the sensor interface device worn by another user. FIG. 3A illustrates the reception of a message using functional ink as described above. A message may be transmitted via an electronic device. Upon reception, the message may be transduced into a chemical or biological signal that the tattoo created with functional ink on the receiving entity senses triggering the appearance of a filled heart. Other transformations on the tattoo may be also possible such as changes in temperature, humidity, texture or rigidity of the heart shape.

Figure 3B:
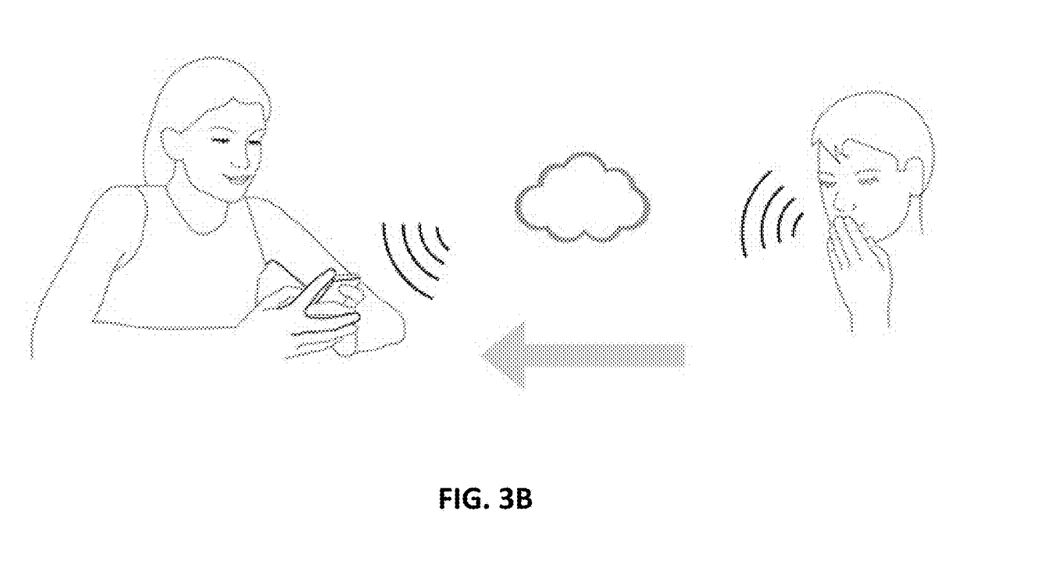

FIG. 3B illustrates the transmission of a message via interaction with a tattoo or set of tattoos created with programmable materials (e.g., one or more functional inks). The sender may be wearing a sensor interface device 100 (e.g., formed as tattoo adhering to skin), which may sense when he touches his lips to the sensor interface device 100 on his hand. Sensing may occur in a number of ways, including the sensing of a common biochemical analyte found in a human mouth or a unique signature of biochemical analytes found in the specific sender's mouth. Other methods may include sensing of pressure applied on both lips and fingers (e.g., where tattoos are worn on all parts). The tattoo or tattoos may then transduce the sensed signal into an electrical one that is transmitted to the receiving entity via a conventional electronic system. A variant of this scenario would allow the application of a tattoo on any surface (e.g., on the body or otherwise).

Figure 3C:
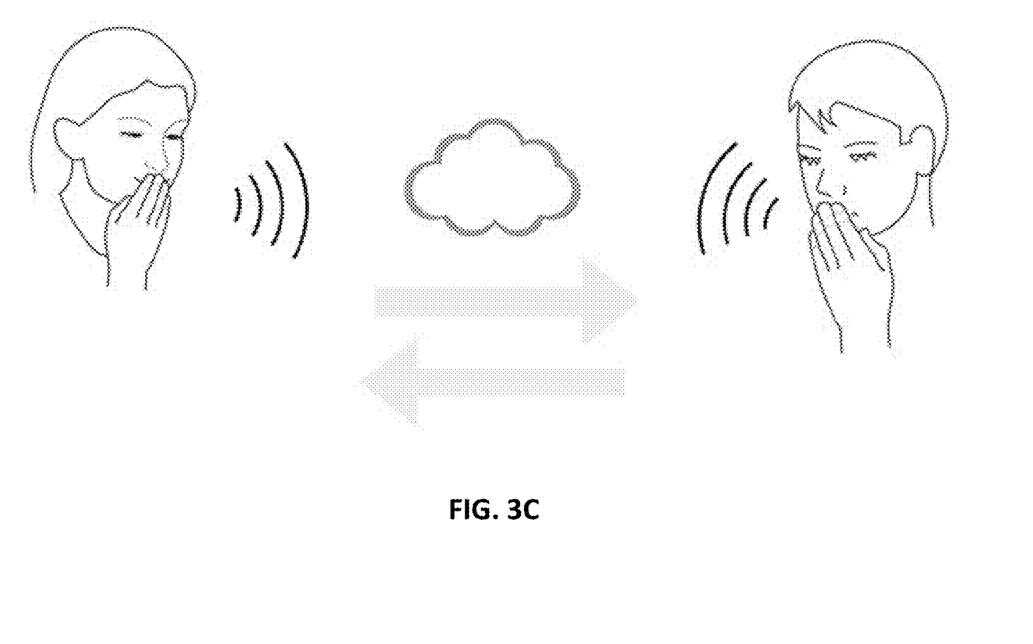

FIG. 3C illustrates the transmission and reception of a message via interaction with a tattoo or set of tattoos created with programmable materials on both sending and receiving entities. In addition to the functionalities described with respect to FIGS. 3A and 3B, others may include sensing of specific changes in shape of the sender's lips, humidity, temperature, smell, etc., and recreating them in the receiver's sensor interface device 100 (e.g., as worn on skin) by an actuating mechanism that changes texture, temperature, humidity, or other characteristics as described herein. An electronic system may also be used to communicate signals (e.g., transduced electrical signals).

Figure 3D:
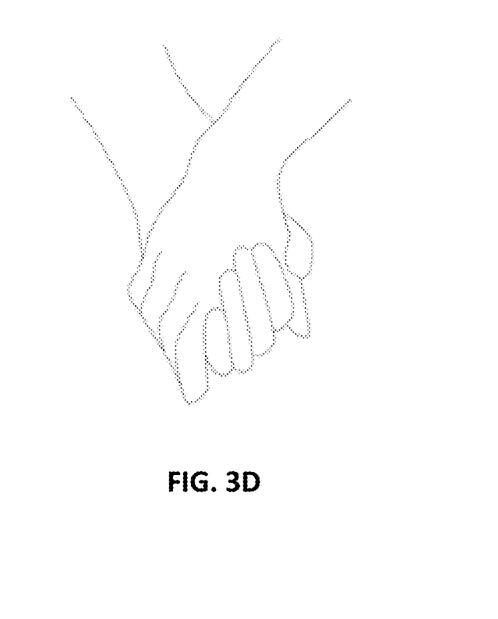

FIG. 3D illustrates the transmission and reception of a message relying solely on the use of a programmable materials. Here, two communicating entities may hold their hands together. Sensor interface devices 100 (e.g., temporary tattoos) with functional ink(s) may sense each other and exchange information with each other. Information transmitted may include the direct measure of analytes of interest, a compounded measure of the sender's health via a particular concentration of an artificial analyte (e.g., a harmless salt that the tattoo releases based on a number of variables such as hydration, glucose, UV light exposure, etc.), or other conditions.

A variant of this scenario may include filtering certain information being sent based on the unique signature of analytes that the sending sensor interface device 100 is sensing from the receiving entity. An optional electronic system may be coupled as a wearable device that provides additional information about the exchange. Another variant may include having a secondary tattoo that is used as a display, while the tattoo on the palm of the hand (or on the lips if they were to kiss) may be used for sensing. The primary and secondary tattoos may communicate via a number of ways, including printed microfluidic channels or electronically as described herein. Use scenarios for this communication method include: health care workers who track infection sources and spread throughout a hospital or healthcare facility, detection and spread of sexually transmitted diseases (or lack thereof) between two partners or potential partners.

Figure 4:
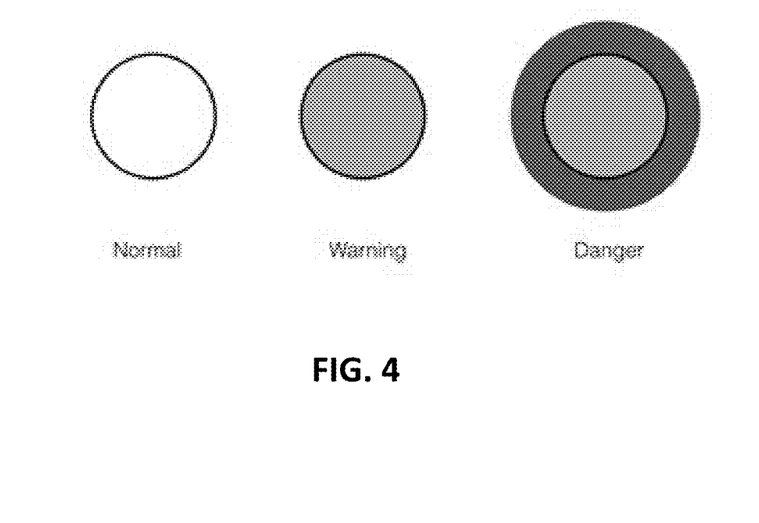
FIG. 4 illustrates exemplary indicators exhibited by the sensor interface device.

FIG. 4 illustrates exemplary indicators exhibited by the sensor interface device 100. In the implementation illustrated, alerts may be provided as to incremental changes in their health. A first state may reflect normalcy (e.g., no significant UV radiation exposure currently detected). A second state may warn of a potentially damaging but reversible condition (e.g., significant exposure to UV radiation detected producing short-lived and reversible effects). A third state may be indicative of significant and/or chronic effects in the user's health (e.g., continuous exposure to UV radiation producing more permanent changes such as suppression of the immune system, damage to the eyes, premature aging, and cancer). Such a progression may be used to generate alerts to reversible versus more permanent changes with respect to a variety of conditions of interest. For example, alerts may concern alcohol consumption above a certain threshold versus early symptoms of cirrhosis. Another example may warn of a current level of dehydration detected versus symptoms of chronic dehydration, such as an acid-alkaline imbalance or a compounded measure of multiple symptoms associated with chronic dehydration. Another example may include notifications regarding higher than normal levels of cholesterol (or a chemical compound associated with higher than normal levels of cholesterol) versus the detection of chronic cholesterol-related symptoms such as coronary artery disease.

Figure 5:
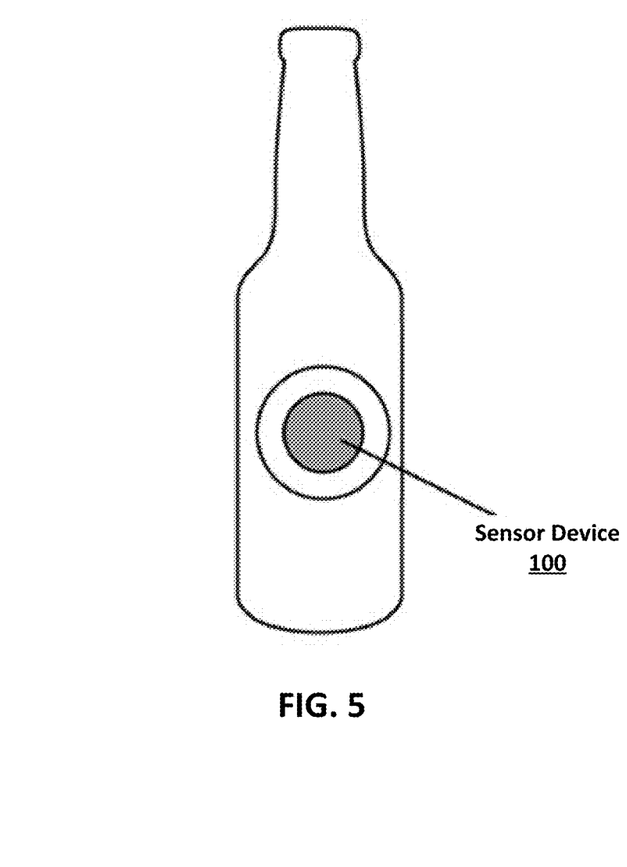
FIG. 5 illustrates an exemplary form in which the sensor interface device may be used.

FIG. 5 illustrates an exemplary form in which the sensor interface device 100 may be provided and used. As illustrated, the sensor interface device 100 may be provided as a temporary tattoo to be worn on the skin to detect alcohol consumption. Such sensor interface device 100 may be given in tandem with another product (e.g., bottle of beer) in a variety of form-factors, such as labels, stickers, promotional material, etc. The illustrated example of a beer bottle and alcohol-sensing tattoo (i.e., sensor interface device 100) that can be peeled off and worn by the user. In this scenario, the external bottle condensation can help dilute the tattoo adhesive (so it comes off of the bottle more easily), while also helping with the tattoo application, since the adhesive can then be applied to the user skin.

FIG. 6 illustrates an exemplary computing system 600 that may be used to implement an embodiment of the present invention. The computing system 600 of FIG. 6 includes one or more processors 610 and memory 620. Main memory 620 stores, in part, instructions and data for execution by processor 610. Main memory 620 can store the executable code when in operation. The system 600 of FIG. 6 further includes a mass storage device 630, portable storage medium drive(s) 640, output devices 650, user input devices 660, a graphics display 670, and peripheral devices 680.

The components shown in FIG. 6 are depicted as being connected via a single bus 690. However, the components may be connected through one or more data transport means. For example, processor unit 610 and main memory 620 may be connected via a local microprocessor bus, and the mass storage device 630, peripheral device(s) 680, portable storage device 640, and display system 670 may be connected via one or more input/output (I/O) buses.

Mass storage device 630, which may be implemented with a magnetic disk drive or an optical disk drive, is a non-volatile storage device for storing data and instructions for use by processor unit 610. Mass storage device 630 can store the system software for implementing embodiments of the present invention for purposes of loading that software into main memory 620.

Portable storage device 640 operates in conjunction with a portable non-volatile storage medium, such as a floppy disk, compact disk or Digital video disc, to input and output data and code to and from the computer system 600 of FIG. 6. The system software for implementing embodiments of the present invention may be stored on such a portable medium and input to the computer system 600 via the portable storage device 640.

Input devices 660 provide a portion of a user interface. Input devices 660 may include an alpha-numeric keypad, such as a keyboard, for inputting alpha-numeric and other information, or a pointing device, such as a mouse, a trackball, stylus, or cursor direction keys. Additionally, the system 600 as shown in FIG. 6 includes output devices 650. Examples of suitable output devices include speakers, printers, network interfaces, and monitors.

Display system 670 may include a liquid crystal display (LCD) or other suitable display device. Display system 670 receives textual and graphical information, and processes the information for output to the display device.

Peripherals 680 may include any type of computer support device to add additional functionality to the computer system. For example, peripheral device(s) 680 may include a modem or a router.

The components contained in the computer system 600 of FIG. 6 are those typically found in computer systems that may be suitable for use with embodiments of the present invention and are intended to represent a broad category of such computer components that are well known in the art. Thus, the computer system 600 of FIG. 6 can be a personal computer, hand held computing device, telephone, mobile computing device, workstation, server, minicomputer, mainframe computer, or any other computing device. The computer can also include different bus configurations, networked platforms, multi-processor platforms, etc. Various operating systems can be used including Unix, Linux, Windows, Macintosh OS, Palm OS, and other suitable operating systems.

What is claimed is:

1. A dynamic sensor device comprising:
   a signal interface that includes a first portion of the signal interface including a radio transceiver configured to receive a user input sent over a communication network, and a second portion of the signal interface configured to release at least one predetermined signal of a plurality of predetermined signals based on the user input, wherein the user input is a message from a remote user device;
   a reaction portion comprising a biological-based or chemical-based ink that reacts in response to the at least one predetermined signal released by the second portion of the signal interface to yield a first optically observable reaction and a porous membrane layer comprising an adhesive substrate attachable to skin, wherein the reaction portion is further configured to receive a stimulus of interest from a physical action from a wearer to yield a second reaction; and
   an electrode adjacent to the reaction portion that detects the first reaction by the biological-based or chemical-based ink in the reaction portion in response to the at least one predetermined signal or the second reaction in response to the physical action from the wearer and generates a detection signal upon detection of the first reaction or the second reaction, the radio transceiver of the signal interface emitting a communication signal to the remote user device based on the electrode detecting the first or the second reaction.

2. The dynamic sensor device of claim 1, wherein the first reaction or the second reaction by the biological-based or chemical-based ink includes a change in an electronic state that is detectable by the electrode.

3. The dynamic sensor device of claim 2, wherein an extent of the change in the electronic state correlates to a measurement of the at least one predetermined signal to which the biological-based or chemical-based ink reacts.

4. The dynamic sensor device of claim 3, wherein the detection signal generated by the electrode indicates the extent of the change.

5. The dynamic sensor device of claim 1, further comprising a signal conditioning circuit that transduces the detection signal from the electrode.

6. The dynamic sensor device of claim 1, further comprising a microcontroller that modifies the detection signal from the electrode to yield a modified detection signal.

7. The dynamic sensor device of claim 6, wherein the communication signal emitted by the radio transceiver of the signal interface is further based on the modified detection signal by the microcontroller.

8. The dynamic sensor device of claim 7, wherein the modified detection signal is based on an analysis by the microcontroller, the analysis regarding the first reaction or the second reaction by the biological-based or chemical-based ink.

9. The dynamic sensor device of claim 7, wherein the modified detection signal is based on preprogrammed settings of the microcontroller.

10. The dynamic sensor device of claim 9, wherein the preprogrammed settings are based on previous analyses by the microcontroller.

11. The dynamic sensor device of claim 9, wherein the preprogrammed settings are customized based on the user input received by the radio transceiver of the signal interface.

12. The dynamic sensor device of claim 1, wherein the biological-based or chemical-based ink is disposed in a pattern within the reaction portion, and wherein the first reaction by the biological-based or chemical-based ink in response to the at least one predetermined signal includes a visual change to the pattern.

13. The dynamic sensor device of claim 12, wherein the pattern is recognizable by a camera or an electronic reader.

14. The dynamic sensor device of claim 1, wherein the first reaction or the second reaction by the biological-based or chemical-based ink includes an olfactory change or a tactile change.

15. The dynamic sensor device of claim 1, wherein the biological-based or chemical-based ink is disposed in the reaction portion in a manner as to come into contact with the at least one predetermined signal when the at least one predetermined signal is present in at least one of wearer skin, environment surrounding the reaction portion, and a foreign object that contacts the reaction portion.

* * * * *